United States Patent [19]

Swan

[11] Patent Number: 5,256,660
[45] Date of Patent: Oct. 26, 1993

[54] SYNTHETIC BUFFER COMPOSITION FOR CLINICAL USE

[75] Inventor: Henry Swan, Lakewood, Colo.

[73] Assignee: Henry Swan II Trust, Lakewood, Colo.

[21] Appl. No.: 852,659

[22] Filed: Mar. 17, 1992

Related U.S. Application Data

[63] Continuation-in-part of Ser. No. 683,241, Apr. 10, 1991, abandoned, which is a continuation-in-part of Ser. No. 383,929, Jul. 21, 1989, abandoned, which is a continuation-in-part of Ser. No. 132,594, Dec. 14, 1987, abandoned.

[51] Int. Cl.$^5$ .................. A61K 31/185; A61K 31/495; A61K 31/535
[52] U.S. Cl. .................. 514/238.8; 514/255; 514/578
[58] Field of Search ............ 514/238.8, 255, 578

[56] References Cited

U.S. PATENT DOCUMENTS

| | | | |
|---|---|---|---|
| 4,383,043 | 5/1983 | Denney et al. | 436/74 |
| 4,548,817 | 10/1985 | Filley et al. | 424/127 |

FOREIGN PATENT DOCUMENTS 341793  11/1989  European Pat. Off. .

OTHER PUBLICATIONS

Journal of the American Medical Association, Oct. 16, 1991 Issue, pp. 2121–2126, Fulvio Kette, et al., "Buffer Solutions May Compromise Cardiac Resuscitation by Reducing Coronary Perfusion Pressure".

Manzoni et al., Chem Abstracts vol. 113, No. 37387j (1989).

Eagle, Science, vol. 174, pp. 500–503 (1971).

Butler, *Ionic Equilibrium: A Mathematical Approach*, Addison-Wesley Pub. Co., Inc., (1964), pp. 145–147.

Waters et al., "Spontaneous Lactic Acidosis", Am. J. Med., 1963, 35:781–793.

Kaye, R., "Diabetic Ketoacidosis-The Bicarbonate Controversy", J. Pediat., 1975, 87:156–159.

Luft et al., "Lactic Acidosis in Biguanide-Treated Diabetics: A Review of 330 Cases", Diabetologia, 1978, 14:75–87.

Garella et al., "Severity of Metabolic Acidosis as a Determinate of Bicarbonate Requirements", N. Engl. J. Med., 1973, 289:121–126.

Hazard, P. and J. Griffin, "Calculation of Sodium Bicarbonate Requirement in Metabolic Acidosis", Am. J. Med. Sci., 1982, 18–22.

Ostrea, et al., "The Influence of Bicarbonate Administration on Blood pH in a 'Closed System': Clinical Implications", Fetal Neonat. Med., 1972, 80:671–680.

Arieff et al., "Pathophysiology of Experimental Lactic Acidosis in Dogs", Am. J. Physiol., 1980, 239:F135–142.

Arieff et al., "Systematic Effects of NaHCO$_3$ in Experimental Lactic Acidosis in Dogs", Am. J. Physiol., 1982, 242:F586–591.

Graf et al., "Metabolic Effects of Sodium Bicarbonate in Hypoxic Lactic Acidosis in Dogs", Am. J. Physiol., 1985, 249:F630–635.

Graf et al., "Evidence for a Detrimentla Effect of Bicarbonate Therapy in Hypoxic Lactic Acidosis", Science, 1985, 227:754–756.

Kindig, N. and G. Filley, "Intravenous Bicarbonate May Cause Transient Intraceullar Acidosis", Chest, 1983, 83:712.

(List continued on next page.)

*Primary Examiner*—Mukund J. Shah
*Assistant Examiner*—Philip I. Datlow
*Attorney, Agent, or Firm*—Carol W. Burton; Ralph F. Crandell

[57] ABSTRACT

Methods of administering aqueous synthetic buffer compositions of an N-substituted aminosulfonic acid and a sodium salt of a different substituted aminosulfonic acid suitable to treat oligemic, respiratory and metabolic acidosis are disclosed. Methods of administering aqueous synthetic buffer compositions of a different N-substituted aminosulfonic acid, a sodium salt of an N-substituted aminosulfonic acid and tris(hydroxymethyl)aminomethane which may be similarly employed are also disclosed.

32 Claims, 4 Drawing Sheets

OTHER PUBLICATIONS

Nahas, G., "The Pharmacology of TRIS (Hydroxymethyl) Aminomethane (THAM)", Pharmacol. Rev., 1982, 14:447-472.

Bleich et al., "TRIS Buffer (THAM) An Appraisal of its Physiologic Effects and Clinical Usefulness", N. Engl. J. Med., 1966, 274:782-787.

Strauss, J., "TRIS (Hydroxymethyl) Amino-Methane (THAM): A Pediatric Evaluation", Pediatrics, 1968, 41:667-689.

Good et al., "Hydrogen Ion Buffers for Biological Research", Biochem., 1966, 5:467-477.

Ferguson et al., "Hydrogen Ion Buffers for Biological Research", Anal. Biochem., 1980, 104:300-310.

Belzer et al., "A New Perfusate For Kidney Preservation", Transplantation, 1982, 33:322-323.

J. S. Gillespie, et al., "Adverse Effects of Tris Hydrochloride, a Commonly Used Buffer in Physiological Media", J. Physiol., 1976, 259:561-73.

S. A. Kaplan, "Tris (Hydroxymethyl) Aminomethane (THAM)-A New Buffer for Therapeutic Use", Am. J. Dis. Child., 1962, 103:1-3.

H. Swan, "Metabolic Rate, Temperature and Acid-Base Control: The Best Strategy and Our Needs to Achieve It", J. Extra-Corporeal Tech., vol. 17(2), pp. 65-73 (1985).

H. Swan, "The Importance of Acid-Base Management for Cardiac and Cerebral Preservation During Open Heart Operations", Surg., Gyn. & Obstet., vol. 158, pp. 391-414 (1984).

Swan, 1984 and H. Swan, "The Hydroxyl-Hydrogen Ion Concentration Ratio During Hypothermia", Surg., Gyn. & Obstet., vol. 155, pp. 897-912 (1982).

H. Swan et al., "A Study of Large Infusions of Bicarbonate Containing Electrolyte Solution", Surg., Gyn. & Obstet., vol. 137, pp. 26-30 (1973).

Durst, R. A. and Staples B. R., "Tris/Tris:HCl: A Standard Buffer for Use in the Physiologic pH Range", Clin. Chem., 1972, 18:206-208.

Chemical Abstracts: vol. 96:195977m (1982), Cui et al.

Chemical Abstracts: vol. 68:46235n (1968), Frackowaik et al.

Biological Abstracts: vol. 82:1963 (1960), Balmaceda et al.

Chemical Abstracts: vol. 104:101284s (1986), Hegetschweisen et al.

Chemical Abstracts: vol. 80:46248s (1974), Husberg.

SYNTHETIC BUFFER COMPOSITION FOR CLINICAL USE

RELATED APPLICATIONS

This is a continuation-in-part of U.S. patent application Ser. No. 07/683,241 filed Apr. 10, 1991, now abandoned, which is a continuation-in-part of U.S. patent application Ser. No. 07/383,929 filed Jul. 21, 1989, now abandoned, which is a continuation-in-part of U.S. patent application Ser. No. 07/132,594 filed Dec. 14, 1987, now abandoned, each parent application being hereby incorporated herein by reference.

FIELD OF THE INVENTION

This invention relates to synthetic buffer compositions, methods of making same and methods of using same. More specifically, this invention relates to synthetic buffer compositions finding particular but not exclusive utility in the treatment of disturbed metabolism in vertebrates. Even more specifically, this invention relates to aqueous buffering solutions finding particular but not exclusive utility in the treatment of disturbed metabolism in humans associated with disease, trauma or manipulative procedures.

BACKGROUND OF THE INVENTION

Stabilization and preservation of hydrogen ion concentration in both intra-cellular and extra-cellular body fluids is critical to the health of vertebrates. Considerable attention and scientific study have been devoted to this crucial aspect of maintaining internal homeostasis in humans.

Chemical substances which undergo reversible protonation serve as hydrogen ion buffers. Three chemical systems are primarily involved in vertebrates:

1) the $CO_2$-$HCO_3$ balance;
2) the protein zwitterion system, which is mutually dependent on the $CO_2$-$HCO_3$ balance and which includes contributions made by the dissociation of the imidazole moiety of the histidine component of plasma proteins and hemoglobin; and
3) the $PHO_3/PO_4$ phosphate buffer system. Of these three chemical systems, the phosphate buffer system is the least effective, primarily because of the phosphate buffer system's inefficiency as a buffer above pH 7.2, and also because excessive phosphate causes undesirable side effects. For these reasons and others, phosphate buffers have had very limited clinical utility.

The use of hypothermia in cardiovascular surgery in the early 1950's necessitated an understanding of the relationship between body temperature and normal acid-base equilibria. One critical factor in the relationship between body temperature and pH involves dissociation constants (pK), which change with temperature. This change is substance-specific and is quite variable among different substances.

The change in pK of water is the prime determinant of the pH of neutrality in all living tissues because living tissue is mostly water. As tissue temperature decreases the dissociation of water therein decreases, the pH increases and the pH of neutrality rises. The term "pKa" describes the midpoint of the effective pH range of a given buffer composition.

Buffers are generally efficient only in narrow pH ranges which depend, in part, on their dissociation constants. For example, tris(hydroxymethyl) aminomethane, referred to herein as TRIS, is efficient in the pH range of 7.8 to 8.6, protein buffers are efficient in the range of 7.2 to 7.8 and bicarbonate is efficient in the range of 6.1 to 6.6.

In vertebrate tissue, the intra-cellular pH is regulated so that the hydroxyl ion concentration [$OH^-$] is equal to hydrogen ion concentration [$H^+$], making the ratio of the concentration of $OH-$ to $H+$ equal to 1. While a concentration ratio of 1 defines the pH of neutrality of water (pN), the pH of neutrality varies with temperature. Thus, pN at 37° C. is about 6.8, at 27° C. is about 6.95, and at 17° C. is about 7.17. It is significant to note, however, that the blood and other fluids circulating in the body maintain a pH higher than pN by a factor k which is species specific. Thus, the pH of blood is pN+k. The cell membranes in humans regulate the k value to equal 0.6 pH units.

It is important to understand the relationship of cells and body fluids to pN at various temperatures to evaluate buffer efficiency because the pK of the buffer must rise as temperature falls so that the buffer will remain efficient throughout the range of the rising pH of cell and body fluids. In view of the importance of this relationship, many skilled in the art consider that the buffer pK should parallel pN at about 0.6 pH units higher to maintain efficiency. Unfortunately, the pK of the bicarbonate and phosphate buffers do not change proportionately to that of pN and, as cooling progresses, both buffers are in a pH range increasingly remote from the tissue pH range in which they are expected to work.

In contrast, the pK of imidazole, the buffer moiety of histidine almost superimposes the changing pN of water as temperature lowers. This explains the value of the histidine-rich plasma proteins and hemoglobin as buffers in human tissues and fluids, not only at homothermia but also at all viable hypothermic temperatures.

A convenient and useful designation concerning the buffering capacity of a buffer solution is the designation of the buffer's Van Slyke buffer value $\beta$. The Van Slyke buffer value $\beta$ indicates the resistance of the buffer to change in pH upon addition of an acid or base, and is defined by the ratio $\Delta B/\Delta pH$, where B is the increment of completely dissociated base or acid in gram-equivalents per liter required to produce a unit change in pH. Thus, Slykes are the units of buffer strength ($\beta$) derived form the formula $\beta = B/1pH$, where B is millimoles of 1N acid or base. The non-bicarbonate buffer value of human blood is estimated at 28 Slykes of which 8 are due to plasma proteins and 20 are due to hemoglobin.

In healthy persons the acid-base equilibria of tissue is maintained largely by the interplay of the bicarbonate and protein buffer systems in accordance with the following relationships:

Protein buffer systems, denoted herein as "Pr−", include hemoglobin which serves as a reservoir of $H+$ ions, accepting or releasing $H+$ ions as equilibria dictate. In the event of hypothermia, bicarbonate becomes ineffective as a buffer and hemoglobin is the most effective buffering mechanism in the body.

A variety of clinical conditions threaten the acid-base balance. Acute acidosis can result from circulatory or respiratory insufficiencies or metabolic disorders. Circulatory insufficiency can be caused by coronary occlusion with myocardial hypoxia, traumatic wound of the heart, constrictive pericarditis or toxic myocarditis, hemorrhage, general body hypothermia, occlusive vascular disease, severe diarrhea and any severe trauma causing diminution in circulating blood volume. Respiratory insufficiency can result from thoracic wounds or injury, pulmonary inflammation, emphysema or a pulmonary embolism. Metabolic acidosis can result from diabetes, renal failure, inborn metabolic disorders or hepatic insufficiency.

Some acidotic conditions, for example severe diarrhea, can be efficiently treated by salt and water replacement. However most acidotic conditions cannot be so treated efficiently. One such condition is acidosis which universally accompanies cardiopulmonary bypass surgery with circulatory arrest in infants and adults. A safe, efficient buffer solution for use in cardiopulmonary bypass surgery has yet to be marketed.

During hypothermic cardiopulmonary bypass surgery it is desirable to dilute the blood significantly for rheological reasons. For instance, the heart-lung machine is primed with crystalloid solutions often containing blood to augment oxygen transport and thus to decrease perfusion rate. Recently, increasingly colder temperatures have been induced to improve myocardial tolerance to ischemia and to diminish body tissue oxygen requirements. In adults, as the crystalloid prime mixes with the patient's blood, the resulting perfusion fluid has an adequate oxygen transport capability but loses significant buffering capacity due to a diminished hemoglobin and plasma concentration. In infants when crystalloid prime is used without the addition of blood, the resulting fluid is an inadequate oxygen transport medium at temperatures above 15° C. Under these conditions, hypoxia, plus lack of buffering capacity, leads to the lactic acidosis of hypoxia. As a result, acidosis is a fairly common occurrence in cardiac operating rooms especially because of the decreased use of blood bank blood due to the risk of AIDS. Since lack of buffer capacity contributes to lactic acidosis in hypoxia, a pump prime should contain a buffer even if the oxyhemoglobin content is lowered.

Since World War I $NaHCO_3$ solution has increasingly become the only buffering agent available. With the vigorous methods of resuscitation currently in vogue using pre-loaded syringes, many patients with circulatory crises, severe trauma or other causes of lactic acidosis are receiving large doses of $NaHCO_3$. In some cases, the large doses of $NaHCO_3$ amount to an overload. The clinical evidence that such therapy is beneficial is extremely scanty; on the contrary, the current literature increasingly warns of the danger of such therapy. It has even been noted that no apparent clinical relationship exists between the amount of bicarbonate administered and eventual patient outcome.

In patients with respiratory problems, the failure to eliminate the $CO_2$ may cause serious acidosis with dangerous levels of $P_{CO_2}$, the partial pressure of $CO_2$ in the blood. When sodium bicarbonate is given intravenously, the $CO_2$ generated diffuses more readily than bicarbonate across cell membranes and into the cerebrospinal fluid, thus potentially augmenting cerebral damage during hypoxic episodes. Hyperosmolality resulting from concentrated bicarbonate infusion can also cause myocardial arrhythmias, low capillary flow and decreased myocardial contractility.

The high sodium content of bicarbonate causes extracellular sodium retention when excessive amounts cannot be excreted. Excessive sodium retention results in excessive water retention, which in turn results in tissue edema and malfunction of various organs. Moreover, blood volume increases and oxygen transfer in impeded, thus increasing circulatory demand which increases the work load on the heart. In addition, the sodium overload can cause a delayed metabolic alkalosis which can lead to tetany and convulsions. In infants, this condition is thought to contribute to neonatal intracranial hemorrhage.

The absence of clinical evidence supporting the use of bicarbonate in the treatment of ketoacidosis, hypoxic lactic acidosis or circulatory arrest is not surprising in light of the buffering deficiencies of $NaHCO_3$. Its pKa varies with temperature between 6.1 at 37° C. and 6.2 at 17° C. Thus, bicarbonate's effective buffer range of 5.7 to 6.8 lies almost totally outside the pH range of most clinical problems and its low $\Delta pk/°C$. renders it ineffective in hypothermic states.

A recent series of papers, Arieff et al., "Pathophysiology of Experimental Lactic Acidosis in Dogs", Am J. Physiol., 1980, 239: F 135–142; Arieff et al., "Systemic Affects of $NaCHO_3$ in Experimental Lactic Acidosis in Dogs", Am. J. Physiol. 1982, 242: F 586–591; Graf et al. "Metabolic Effects of Sodium Bicarbonate in Hypoxic Lactic Acidosis in Dogs", Am. J. Physiol., 1985, 249:F 630–635; and Graf et al. "Evidence for a Detrimental Effect of Bicarbonate Therapy in Hypoxic Lactic Acidosis", Chest, 1983, 83: 712–716, describe two animal models of lactic acidosis in which the efficiency of sodium bicarbonate therapy is examined. These experimental studies clearly indicate that under conditions of induced metabolic or hypoxic lactacidemia, intravenous administration of sodium bicarbonate worsens rather than alleviates the metabolic and hemodynamic consequences.

In an attempt to avoid the profound acute elevations in $P_{CO_2}$ induced by intravenous bicarbonate, a salt solution containing 0.33M bicarbonate and 0.33M carbonate has been proposed. While this solution, termed "carbicarb," diminishes or ablates the immediate rise in $P_{CO_2}$, after 15 minutes the carbicarb has the same effect achieved by infusing an equal amount of bicarbonate solution. Moreover, the sodium overload is the same and both solutions are ineffective to raise blood pH in experimental shock, lactic acidosis, cardiopulmonary arrest and certain other conditions. A recent study, Kette et al., "Buffer Solutions May Compromise Cardiac Resuscitation by Reducing Coronary Perfusion pressure", JAMA 1991, 266:2121-2126, presents evidence that the previously documented failure of infused bicarbonate and carbicarb to protect intramyocardial pH during porcine cardiac arrest may be due to depression in coronary blood flow caused by the extreme hyperosmolality of these two "buffers" at 2000 milliosmols per liter.

Clearly, the widely used bicarbonate solutions are therapeutically inadequate and are dangerous when used as alkalinizing agents. Unfortunately, there are no proven non-protein buffers currently available for use in clinical therapy.

Although blood and tissue byproduct buffers exist, such as protein buffer substitutes, they are prepared from blood or blood products of other species and therefore contain foreign protein which can cause a hyperimmune response. Moreover, such protein buffer substitutes are expensive and the disposal from the patient's body of degradation products can cause significant problems.

Synthetic buffering agents have also been investigated. One possible synthetic agent, TRIS, received extensive pharmacological investigation and clinical trials in the early 1960's. TRIS potentially can directly neutralize the weak acids of metabolic acidosis. However, TRIS is a strong base with a pH of 10, a pKa of 8.3 at 20° C., and a $\Delta pK/°C$. of about 0.020. The intravenous administration of TRIS causes severe vasospasm, phlebitis and local cellular necrosis. Neutralization with HCl to avoid these complications nullifies TRIS' capacity to buffer carbonic acid and to generate bicarbonate. There is little current clinical, theoretical or experimental evidence supporting a significant therapeutic role for TRIS. Essentially, TRIS has a pKa too high to be effective in the pH range of clinical acidosis. However, because of its high alkalinity and absence of sodium, TRIS might serve as a useful component in a compound with other synthetic buffers.

A family of N-substituted aminosulfonic acids have been synthesized and shown to be potentially useful buffering agents. However, it is believed that none of these synthetic buffering agents have had whole animal toxicity or pharmacological studies performed. It is further believed that these synthetic buffering agents have been used only in tissue culture, virus, enzyme and thermodynamic studies.

In 1966, Good and his associates introduced ten new hydrogen ion buffers, four of which were synthetic zwitterion aliphatic amines derived from taurine or glycine using bromoethanesulfonate. See Good et al., "Hydrogen Ion Buffers for Biological Research," Biochem., 1966, 5:467–477. Later, Ferguson and his colleagues introduced five similar new buffers synthesized from a different source. See Ferguson et al. "Hydrogen Ion Buffers for Biological Research," Anal Biochem, 1980, 104:300–310. These aminosulfonic acid buffers together with other synthetic compounds form a family of about sixteen synthetic buffers each with a known pKa, $\Delta pK°/C$. and neutralization equivalent. A few of these synthetic buffers have been used successfully in laboratories as precise buffers in studies involving enzyme dynamics and virus, bacterial and cell tissue cultures.

As early as 1971, the importance of differences in the pKa of various members of the aminosulfonic acid family in designing tissue culture media with optimal buffering capabilities at different pH levels has been recognized. For example, Eagle H., Science, 1971 174:500–503 showed that three different aminosulfonic acids improved the buffering stability of a 24 millimolar solution of sodium bicarbonate, with sodium phosphate sometimes supplemented. However, of the 16 biological buffers evaluated, 8 were too toxic to use for cell culture in concentrations as low as 0.020M. The other 8 buffers showed significant suppression of growth of certain cell lines. The fact that some of the aminosulfonic acids were cell toxic in extremely low concentration posed a challenge to investigation in the whole animal field of the current invention.

Combinations of two aminosulfonic acids, N-(2-hydroxyethyl)piperazine-N'-(2-ethanesulfonic acid) and 3-(N-morpholino) propanesulfonic acid and their respective sodium salts have also been used to produce very precise pH solutions for use in standardizing pH instruments. See Eur. Pat. Appl RP 341,793, IT Appl. 88/20,560, 13 May 1988, to Manzoni, A. and Belluati, M. This patent discloses aminosulfonic acid in combination with its sodium salt to create a buffer solution with a precise pH but no consideration is given to the effect of temperature on pH nor to any of the biological characteristics needed in a clinical buffer.

Thus, although lactic acidosis is a very common and often fatal clinical disorder, not a single effective therapeutic agent is currently available to prevent or counteract it. Furthermore a buffer composition with a pKa about 7.2 at 25° C. is urgently needed to counteract the myocardial acidosis resulting from hypothermic heart surgery.

While approximately 16 synthetic compounds having buffering capability are commercially available, such synthetic compounds have been used extensively only in laboratory studies as components in buffer compositions to stabilize pH in culture media for cell, bacterial or viral studies. The effect of temperature on the pKa of buffer systems has been completely unaddressed.

It is believed that no attempt has been made to evaluate synthetic buffers in vertebrates, especially humans. It is currently not known whether any members of the family of N-substituted aminosulfonic acids and/or their sodium salts are non-toxic when rapidly administered intravenously to laboratory test animals in large doses. It is not known if compositions of aminosulfonic acids and their salts can be devised to have pH, pKa, $\Delta pk/°C$., osmolality and sodium ion concentration characteristics to treat different forms of clinical hypoxic acidosis specifically and effectively.

It is the principal object of the present invention to produce effective synthetic therapeutic agents suitable for use as buffering agents in vertebrates. It is a further object of the present invention to produce buffering agents suitable for use in vertebrates which can counteract lactic acidosis in vertebrates. It is yet a further object of the present invention to produce buffering agents especially useful for counteracting the myocardial acidosis of hypothermic heart surgery and the generalized lactic acidosis of hemorrhage and traumatic shock.

It is a still further object of the present invention to provide methods for administering a synthetic buffering agent in large doses to counteract lactic acidosis in vertebrates. It is a still further object of the present invention to provide methods for devising synthetic buffering agents suitable for use in counteracting lactic acidosis in vertebrates and having appropriate pH, pKa, $\Delta pK/°C$., osmolality and sodium ion characteristics designed to treat different forms of clinical hypoxic acidosis specifically and effectively.

SUMMARY OF THE INVENTION

A significant aspect of the present invention relates to methods of administering a synthetic buffer composition in vertebrates, especially in humans, to treat safely and effectively differing forms of acidosis encountered clinically. Another significant and specific aspect of the present invention relates to methods of administering a synthetic buffer composition having expanded buffering capacities over a wide range of temperatures when infused into animals and humans, exhibiting improved safety and survivability.

Another significant aspect of the present invention relates to methods of administering an aqueous buffer solution suitable in vertebrates, especially humans, comprising a water or balanced salt solution and one or more N-substituted aminosulfonic acids and a sodium salt of a different N-substituted aminosulfonic acid. Yet another significant aspect of the present invention relates to methods of administering an aqueous buffering solution having the aforementioned characteristics wherein the solution further includes tris(hydroxymethylamineomethane).

DETAILED DESCRIPTION OF THE INVENTION

Hypothermia is widely used in cardiopulmonary bypass surgery. The inventor of the present invention was a pioneer in the use of hypothermia in open heart surgery and in recognizing the importance of maintaining proper acid-base balance during this procedure. Based upon the inventor's studies and those of others, it has been determined that an effective buffering agent for clinical use in humans should have the following attributes:

1. The buffer's temperature coefficient should be similar to that of water (pKw). The pK should approximate pN+0.6 pH, and $\Delta pK/°C$. should be in the range 0.01 to 0.025.
2. The buffer should be biologically inert and neither toxic nor antigenic.
3. The buffer should be highly soluble in water but pass through cellular membranes only with difficulty.
4. The buffer should be stable and not subject to enzymatic degradation.
5. The buffer should contain concentrations of cations or anions normally present in body fluids in levels designed to rectify abnormal concentrations in body fluids.

In regard to these ideal characteristics, it is known that the N-substituted aminosulfonic acids (ASAs) have a $\Delta pK/°C$. similar to that of pKw, and that their strong polarity hinders them from participating in trans-cellular membrane systems. Moreover, since ASAs do not occur naturally in vertebrate biological tissues, their synthetic origin renders them unlikely to function as analogs or competitors with most biological substances.

Contrary to published statements that even in very dilute concentrations ASAs are toxic to cell cultures, experimentation by the inventor which included intravenous injection of ASAs in large, rapidly administered doses into rats resulted in a survival rate of 13 out of 15 rats. Moreover, when an aminosulfonic acid-salt composition embodying the present invention was intermittently administered by coronary infusion during prolonged continuous myocardial hypothermic ischemia in dogs, intramyocardial pH and myocardial ATP levels were maintained at normal levels.

The synthetic buffer compositions suitable for use in clinical applications and embodied in the present invention comprise one or more N-substituted aminosulfonic acids and one or more sodium salt of N-substituted aminosulfonic acids and/or TRIS. The N-substituted aminosulfonic acids are selected from the following group:

N-2-(acetamido)-2-aminoethanesulfonic acid, referred to herein as ACES;

N,N-bis (2-hydroxyethyl)-2-aminoethanesulfonic acid, referred to herein as BES;

3-[N-bis (hydroxyethyl)amino]-2-hydroxypropanesulfonic acid, referred to herein as DIPSO;

N-(2-hydroxyethyl)piperazine-N'-(2-ethanesulfonic acid), referred to herein as HEPES;

N-(2-hydroxyethyl)piperazine-N'-(2-hydroxypropanesulfonic acid) referred to herein as HEPPSO;

3-(N-morpholino)propanesulfonic acid referred to herein as MOPS;

3-(N-morpholino)-2-hydroxypropanesulfonic acid referred to herein as MOPSO;

piperazine-N,N'-bis(2-ethanesulfonic acid) referred to herein as PIPES;

piperazine-N, N'-bis(2-hydroxypropanesulfonic acid) referred to herein as POPSO;

3-[N-tris(hydroxymethylamino]-2-hydroxypropanesulfonic acid referred to herein as TAPSO; and N-tris(hydroxymethyl) methyl-2-aminoethanesulfonic acid referred to herein as TES.

The sodium salt of ACES is referred to herein as NaACES, the sodium salt of BES is referred to herein as NaBES, the sodium salt of DIPSO is referred to herein as NaDIPSO, the sodium salt of HEPES is referred to herein as NaHEPES, the sodium salt of HEPPSO is referred to herein as NaHEPPSO, the sodium salt of MOPS is referred to herein as NaMOPS, the sodium salt of MOPSO is referred to herein as NaMOPSO, the sodium salt of PIPES is referred to herein as NaPIPES, the sodium salt of POPSO is referred to herein as NaPOPSO, the sodium salt of TAPSO is referred to herein as NaTAPSO, and the sodium salt of TES is referred to herein as NaTES.

ACES, BES, DIPSO, HEPES, HEPPSO, MOPS, MOPSO, PIPES, POPSO, TAPSO, TES and TRIS have the structures illustrated on the following two pages.

| | |
|---|---|
| ACES | |
| $H_2NCOCH_2NH_2CH_2CH_2SO_3H$ | $C_4H_{10}N_2O_4S$ |
| BES | |
| $(HOCH_2CH_2)_2=NCH_2CH_2SO_3H$ | $C_6H_{15}NO_5S$ |
| DIPSO | |
| $\begin{array}{c} OH \\ | \\ CH_2-C-CH_2-SO_3H \\ | \\ HOCH_2-CH_2-NH-CH_2-CH_2OH \end{array}$ | $C_7H_{17}NO_6S$ |
| HEPES | |

-continued

DIPSO $$\text{H}_2\text{C}\overset{\overset{\text{CH}_2\text{CH}_2\text{OH}}{|}}{\underset{\underset{\text{CH}_2-\text{CH}_2-\text{SO}_3\text{H}}{|}}{\text{N}}}\text{CH}_2$$

$C_8H_{18}N_2O_4S$

HEPPSO

$C_9H_{20}N_2O_5S$

MOPS

$C_7H_{15}NO_4S$

MOPSO

$C_7H_{15}NO_5$

PIPES

NaO₃SCH₂CH₂N      NHCH₂CH₂SO₃H $C_8H_{18}N_2O_4S_2$

POPSO $C_{10}H_{22}N_2O_8S$

TAPSO $$\text{(HOCH}_2)_3-\text{C}-\overset{\overset{\text{OH}}{|}}{\text{NH}-\text{CH}-\text{CH}_2-\text{CH}_2-\text{SO}_3\text{H}}$$

$C_7H_{17}NO_7S$

TES
(HOCH₂)₃—C—NH—CH₂—CH₂—SO₃H $C_6H_{15}HO_6H$

TRIS
(HOCH₂)₃—C—NH₂

$C_4H_{11}NO_3$

The aqueous buffering solutions of the present invention can be specifically designed for different clinical states or acid-base disorders by using combinations of the synthetic buffers listed above in combination with salts of the synthetic buffers listed above to create a solution with a unique pattern of the important parameters pH, pK, ΔpK/°C., molarity, osmolality and sodium content. The improved aqueous buffering solutions of the present invention can be formulated to be close to the pH of neutrality at various temperatures and therefore administered intravenously to patients without causing vasculitis. The improved aqueous buffering solutions can also be administered in the treatment of acute acidosis due to circulatory or respiratory insufficiency or of metabolic origin. The improved aqueous buffering solutions are also useful as priming fluid for extracorporeal circulatory devices. The aqueous buffering solutions of the present invention can also be used in transurethral irrigation or as irrigating solutions for the treatment of wounds, burns, ocular disturbances or skin diseases. Moreover, the synthetic buffer compositions of the present invention can further be used as a buffer in formulations for topical application such as, for example, with cosmetic applications.

In formulating the improved aqueous buffering compositions of the present invention the sodium salts of N-substituted aminosulfonic acids and/or TRIS can be added in varying amounts in order to create specific and appropriate parameters of pH, pK, ΔpK/°C., molarity, osmolality and sodium ion content. Similarly, water and balanced salt solution can be used alone or in combination to achieve the same purpose. Moreover, since the dissociation constants of the different ASAs have different temperature coefficients, certain ASAs are more appropriate than others for establishing the desired ΔpK/° C. parameter of a compound.

EXAMPLE I

Synthetic buffer compositions of the present invention contain at least one ASA selected from the group consisting of ACES, BES, DIPSO, HEPES, HEPPSO, MOPS, MOPSO, PIPES, POPSO, TAPSO and TES and also contain at least one sodium salt selected from the group consisting of NaACES, NaBES, NaDIPSO, NaHEPES, NaHEPPSO, NaMOPS, NaMOPSO, NaPIPES, NaPOPSO, NaTAPSO and NaTES. The ASA and sodium salt are present in the buffering solution in sufficient quantities so as to produce a buffering solution having a pH of approximately from 7.0 to 7.8 at 25° C., a pKa of approximately from 7.0 to 7.8 at 25° C., a molar strength of from approximately 0.01M to 0.5M, a ΔpK/°C. between about 0.010 and about 0.020, an osmolality preferably not exceeding approximately 500 mOsm and a sodium ion concentration of up to approximately 0.5M.

EXAMPLE II

The synthetic buffer composition described above in Example I is obtained by adding TRIS to the ASA and sodium salt in such quantities as to obtain a buffering solution having the characteristics described in Example I.

EXAMPLE III

The synthetic buffer composition of the present invention having the characteristics described above in Example I is obtained by substituting TRIS for the sodium salt in Example I.

EXAMPLE IV

A method for treating acidosis in a patient comprises the intravenous administration of an aqueous buffering solution containing at least one ASA selected from the group consisting of ACES, BES, DIPSO, HEPES, HEPPSO, MOPS, MOPSO, PIPES, POPSO, TAPSO and TES and also containing at least one sodium salt selected from the group consisting of NaACES, NaBES, NaDIPSO, NaHEPES, NaHEPPSO, NaMOPS, NaMOPSO, NaPIPES, NaPOPSO, NaTAPSO and NaTES. TRIS may be substituted, in all or in part for the sodium salt or may be added to the solution of the ASA and the sodium salt. The ASA, sodium salt and/or TRIS should be present in the buffering solution in sufficient quantities so as to produce a buffering solution having a pH of approximately from 7.2 to 7.8 at 37° C., preferably 7.75, a pKa of approximately from 7.4 to 7.8 at 37° C., preferably 7.63, a molar strength of from approximately 0.1 to 0.5M, preferably 0.35M, a $\Delta pK/°C$. between about 0.014 and about 0.020, preferably 0.015, an osmolality of from about 270 to 500 mOsm, preferably 475 mOsm, and a sodium ion concentration of from approximately 0.035 to about 0.35M, preferably 0.140M. The preferred buffering solution for this application contains approximately 47 grams per liter TAPSO, 37 grams per liter NaDIPSO and 3 grams per liter TRIS.

SHOCK DUE TO LIFE-THREATENING HEMORRHAGE

Clinical trials were conducted to determine the effectiveness of various buffers in treating hemorrhagic acidosis thus enabling dogs to recover from life-threatening losses of blood. Six dogs were treated with small infusions of a 0.2M buffer solution prepared with five parts HEPES, four parts NaTAPSO and one part NaMOPS. This solution at 37° C. has a pH of 7.35 and a pKa of 7.31, a sodium ion content of 0.100M and osmolality of approximately 420 mOsm. Four out of the six dogs receiving this treatment survived. Five dogs were treated with a control composition comprising 7.5% NaCl. Use of 7.5% NaCl composition is one currently recommended treatment for traumatic shock. Of the five dogs treated with the control composition, only one dog survived. The survival of 4 of 6 dogs following buffer, as compared to one of 5 treated with salt solution was totally unexpected and is very significant statistically.

Preferred aqueous buffering solutions appropriate for use in a human subjected to trauma and/or hemorrhage in which acidosis results and methods for administration of such solutions are described below in Examples V through VI.

EXAMPLE V

A method for treating general and myocardial acidosis of a patient subjected to trauma and/or hemorrhage, is comprised of intravenous administration of an aqueous buffering solution containing at least one ASA selected from the group consisting of ACES, BES, DIPSO, HEPES, HEPPSO, MOPS, MOPSO, PIPES, POPSO, TAPSO and TES and also containing at least one sodium salt selected from the group consisting of NaACES, NaBES, NaDIPSO, NaHEPES, NaHEPPSO, NaMOPS, NaMOPSO, NaPIPES, NaPOPSO, NaTAPSO and NaTES. TRIS may be substituted, in all or in part for the sodium salt or may be added to the solution of the ASA and the sodium salt. For this application, the ASA, sodium salt and/or TRIS should be present in the buffering solution in sufficient quantities to produce a buffering solution having a pH of approximately from 7.2 to 7.6 at 37° C., preferably 7.35, a pKa of approximately from 7.2 to 7.4 at 37° C., preferably 7.31, a molar strength of from approximately 0.2 to 0.5M, preferably 0.35M, a $\Delta pK/°C$. between about 0.014 and about 0.018, preferably 0.016, an osmolality between about 275 and about 500 mOsm, preferably 430 mOsm, and a sodium ion concentration of from approximately 0.035 to about 0.35M, preferably 0.175M. The preferred buffering solution for this application contains 5 parts of HEPES, 4 parts of NaTAPSO and 1 part NaMOPS dissolved in water so as to produce a 0.35M solution.

EXAMPLE VI

An alternate buffering solution for use in clinical situations in which the buffering solution of Example V is employed preferably contains 4 parts of HEPES, 5 parts of NaDIPSO and 1 part NaMOPS dissolved in water so as to produce a 0.35M solution having a pH of approximately 7.38 at 37° C., a pKa of approximately 7.31 at 37° C., a $\Delta pK/°C$. of approximately 0.015, an osmolality of from approximately 300 to 500 mOsm and a sodium ion concentration of approximately 0.240M.

EXAMPLE VII

Intravenous administration of a buffering solution embodying the present invention may also be used to protect the pH of the blood and the myocardium of a patient suffering acute circulatory insufficiency associated with or due to decreased coronary blood flow. A preferred aqueous buffering solution suitable in such situations contains at least one ASA selected from the group consisting of ACES, BES, DIPSO, HEPES, HEPPSO, MOPS, MOPSO, PIPES, POPSO, TAPSO and TES and also containing at least one sodium salt selected from the group consisting of NaACES, NaBES, NaDIPSO, NaHEPES, NaHEPPSO, NaMOPS, NaMOPSO, NaPIPES, NaPOPSO, NaTAPSO and NaTES. TRIS may be substituted, in all or in part for the sodium salt or may be added to the solution of the ASA and the sodium salt. For this application, the ASA, sodium salt and/or TRIS should be present in the buffering solution in sufficient quantities so as to produce a buffering solution having a pH of approximately from 7.3 to 7.8 at 37° C., preferably 7.35, a pKa of approximately from 7.1 to 7.4 at 37° C., preferably a pKa of approximately 7.25, a molar strength of from approximately 0.2 to 0.5 molar, preferably 0.405 molar, a $\Delta pK/°C$. between about 0.014 and about 0.018, preferably 0.0165, an osmolality between about 285 and about 500 mOsm, preferably 405 mOsm, and a sodium ion concentration of up to approximately 0.150M, preferably 0.105M. The preferred buffering solution for this application contains 6 parts of MOPS, 3 parts of NaHEPES and 1 part TRIS dissolved in water so as to produce a 0.35M solution. The buffering solution should have a buffer value between pH 6.5 and pH 7.5 of approximately 85 Slykes.

EXAMPLE VIII

The buffering solution of Example VII can also be produced in a preferred composition containing 6 parts MOPS and 4 parts TRIS at 0.2M dissolved in a balanced salt solution having a pH about 7.35 and a pK about 7.32 at 37° C., a $\Delta pK/°C$. about 0.017, an osmolality about 475 mOsm, and a sodium ion concentration of 0.14M.

PROTECTION OF ISCHEMIC MYOCARDIUM

One important use for the aqueous buffering solutions of present invention is as a buffering solution for coronary artery perfusion to protect the acid-base balance of the myocardium during the prolonged periods of enforced ischemia during open-heart surgery. More specifically, in "bypass" surgery the myocardium, although partially protected by deep hypothermia, remains anoxic for periods often exceeding two hours. Myocardial metabolism becomes anaerobic and severe lactic acidosis develops. This acidosis activates "reperfusion injury" when circulation is restored, which results in myocardial failure after the surgery. Myocardial failure is the commonest cause of death postoperatively. Current methods of preventing myocardial acidosis are only marginally effective.

Figure 3:
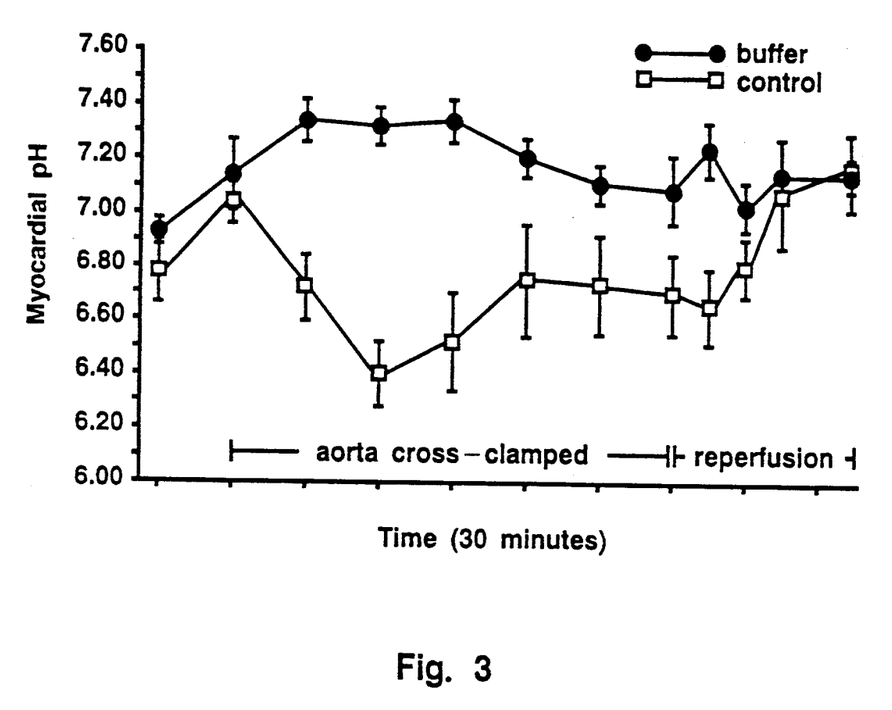
FIG. 3 is a graph containing two curves comparing the buffer capability of an aminosulfonic acid and salt solution with the buffer capability of a bicarbonate solution, each solution given by intermittant coronary infusion, to maintain the intramyocardial pH of a canine heart subjected to 3 hours of total ischemia at 20°.

In view of these circumstances, an experiment was conducted to test the effectiveness of an ASA composition in preventing myocardial acidosis when given by coronary perfusion every 30 minutes during 3 continuous hours of myocardial ischemia at 20° C. FIG. 3 compares the effectiveness of a bicarbonate solution with an ASA solution developed for use with animals in laboratory tests. In particular, the myocardial pH of the animals tested was measured during three hours of cardioplegic arrest for an ASA buffer solution and for a bicarbonate solution control. The ASA solution consists of 7 parts NaMOPS and 3 parts HEPES, dissolved in a standard cardioplegic solution in a strength of 0.2M. At 22° C. the ASA solution has a pH of 7.8, a pka of 7.25, a $\Delta pK/°C.$ of 0.15, an osmolality of 409 mOsm, and sodium ion concentration of 0.235M. The control solution of bicarbonate had 20–30 mEq/L, a pH of 7.8 and pKa of 6.2 at 22° C.

Figure 4:
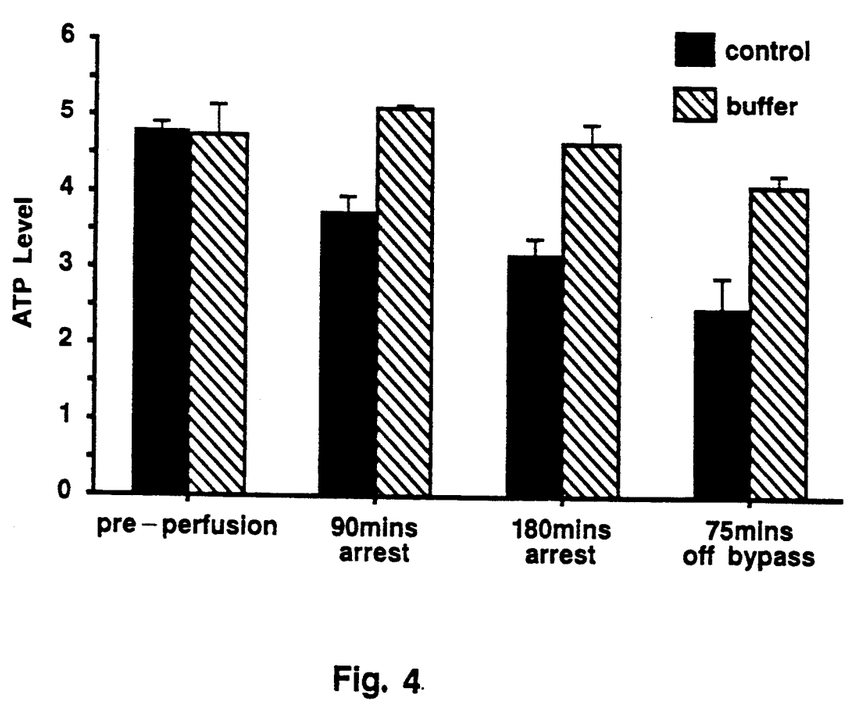
FIG. 4 is a graph containing a block diagram comparing myocardial ATP levels achieved by a buffer as embodied in the present invention with a bicarbonate buffer.

The vertical component of the curves of FIG. 3 represent myocardial pH. The horizontal component of the curves of FIG. 3 represent the time over which the laboratory tests were performed. The significant difference between the pH protection provided by the ASA solution as compared to the bicarbonate solution at every observation point after onset of ischemia indicates the capability of a specifically designed buffer to protect myocardial pH throughout three hours of total ischemia. Such results are not known to have been previously achieved with any buffering solution. Myocardial ATP levels of both the bicarbonate control and the ASA buffer treated animals are illustrated in FIG. 4. In the tests described above involving three hours of myocardial ischemia, measurement of myocardial ATP levels were made pre-ischemia, at 90 and 180 minutes during ischemia, and at 75 minutes off bypass. As is illustrated in FIG. 4, pre-perfusion myocardial ATP stood at the level of 4.77±0.03 in all the dogs in the experiments. In those animals given coronary infusion of ASA buffer, the myocardial ATP was 5.1±0.056 at 90 minutes, and 4.65±0.28 at 180 minutes, the end-ischemic value. Seventy five minutes off-bypass, the ATP level was a healthy 4.02±0.19. In contrast, bicarbonate infusion failed to protect cardiac ATP, which fell successively to 3.76±0.22, 3.18±0.24, and 2.42±0.428 as the experiment proceeded. Each of the ATP levels measured after 90 minutes and 180 minutes of arrest and 75 minutes off bypass are statistically higher than the bicarbonate values, with $p<0.05$. Indeed, the last two levels were so low that without the hearts having reverted within a few hours to effective aerobic metabolism, the subjects would have succumbed to low energy failure.

In summary, prolonged hypothermic myocardial ischemia of dogs treated by intermittent coronary infusion of an 0.2M buffering solution comprising 7 parts NaMOPS and 3 parts HEPES, as compared to treatments using a standard bicarbonate buffering solution, proved that the NaMOPS/HEPES buffer preserved both myocardial pH and ATP levels, whereas the bicarbonate solution achieved neither objective. This almost ideal result was totally unexpected because no known hemoglobin-free cardioplegic programs currently in use in the United States are known to have published equivalent results. Preferred methods employing aqueous buffering solutions of the present invention suitable for use in bypass surgery with humans are described below in Examples IX through XI.

EXAMPLE IX

An aqueous buffering solution used for buffering the pH of the blood and of the myocardium of a hypothermic patient who is undergoing cardiopulmonary bypass surgery, is either administered intravenously, added to the priming fluid of a heart-lung machine or added to a cardioplegic solution for intermittent or continuous coronary perfusion. In the preferred embodiment of an aqueous buffering solution of the present invention suitable for use with hypothermic patients, a composition comprising water and/or balanced salt solution is prepared containing at least one ASA selected from the group consisting of ACES, BES, DIPSO, HEPES, HEPPSO, MOPS, MOPSO, PIPES, POPSO, TAPSO and TES and also containing at least one sodium salt selected from the group consisting of NaACES, NaBES, NaDIPSO, NaHEPES, NaHEPPSO, NaMOPS, NaMOPSO, NaPIPES, NaPOPSO, NaTAPSO and NaTES. TRIS may be substituted, in all or in part for the sodium salt or may be added to the solution of the ASA and the sodium salt. For this application, the ASA, sodium salt and/or TRIS should be present in the buffering solution in sufficient quantities so as to produce a buffering solution having a pH of approximately from 7.4 to 7.8 at 25° C., a pKa of approximately from 7.1 to 7.4 at 25° C., a molar strength of from approximately 0.2 to 0.5M, a $\Delta pK/°C.$ between about 0.014 and about 0.018, an osmolality from approximately 275 to 500 mOsm, and a sodium ion concentration of from approximately 0.10 to 0.40M.

EXAMPLE X

A preferred buffering solution having constituents described above in Example IX is administered by coronary infusion, preferably every 15 to 20 minutes, contains 3 parts HEPES and 7 parts NaMOPS dissolved in a cardioplegic solution so as to obtain a buffering solution of approximately 0.20M concentration and having a pH of approximately 7.75, a pKa of about 7.25, a $\Delta pK/°C.$ of approximately 0.0155, an osmolality of approximately 485 mOsm and a sodium ion concentration of approximately 0.28M.

EXAMPLE XI

A preferred buffering solution having constituents described above in Example IX is added to the priming fluid of a heart-lung machine and preferably contains 4 parts TAPSO, 5 parts NaDIPSO and 1 part TRIS in a balanced salt solution so as to obtain a buffering solution of approximately 0.25M concentration, having a pH of approximately 7.5, a pKa of about 7.5, a $\Delta pK/°C.$ of approximately 0.0175, an osmolality of approximately 476 mOsm and a sodium ion concentration of approximately 0.315M.

The synthetic buffer compositions of the present invention and the methods employing the aqueous buffering solutions as described above in Examples I through XI were developed after obtaining certain unexpected results in various laboratory studies.

Figure 1:
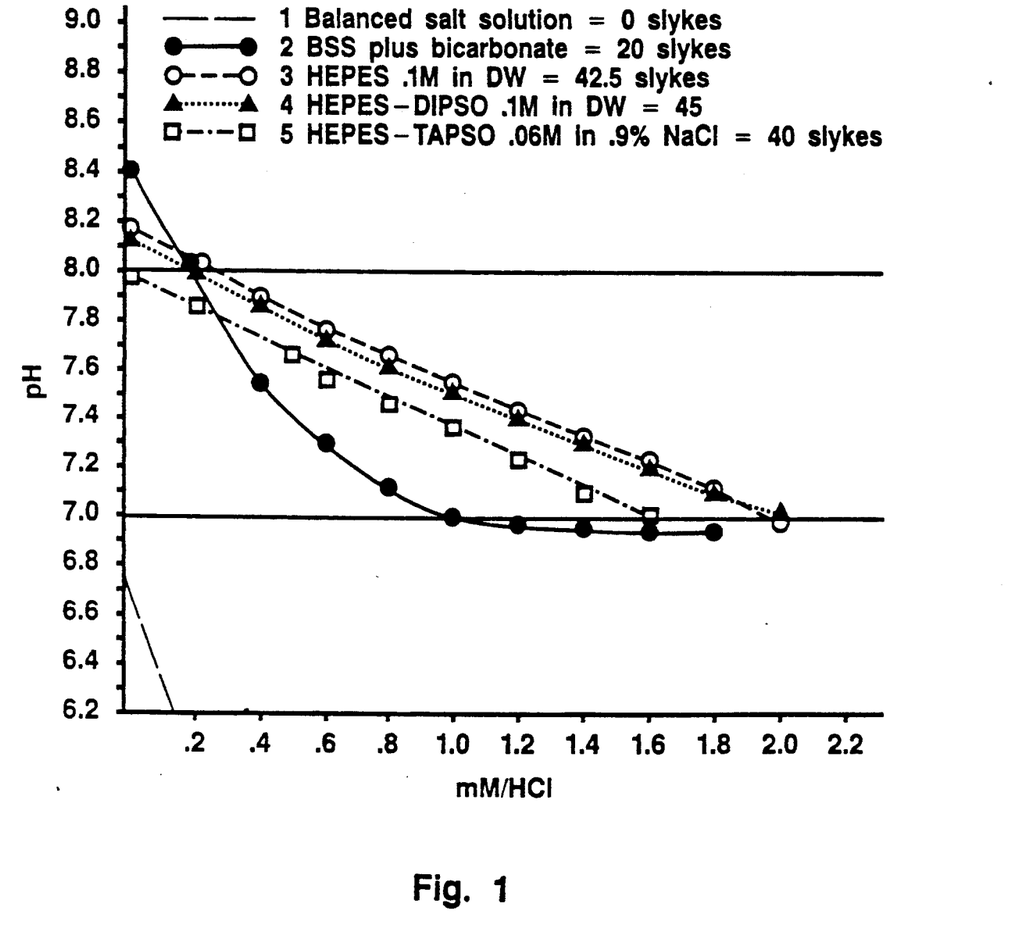
FIG. 1 is a graph containing five curves comparing the buffer strength of three aminosulfonic acid and salt buffers to the buffer strength of a sodium bicarbonate solution and the buffer strength of a balanced salt solution.

A preliminary test was performed to compare the buffering strength of ASAs with that of bicarbonate and to study the effective buffering range of a mixture of an aminosulfonic acid with sodium salts of different aminosulfonic acids compared to each component alone. FIG. 1 contains five curves which serve to illustrate the buffering action of five solutions: (1) HEPES and NaHEPES dissolved in water in equal proportions to achieve a 0.1M solution; (2) 0.06M HEPES and 0.04M DIPSO dissolved in water to achieve a 0.1M solution; (3) HEPES and NaTAPSO dissolved in water in equal proportions to achieve a 0.06M solution; (4) a solution of Plasmalyte A containing 22.5 milliequivalents of $NaHCO_3$ per liter; and (5) a balanced salt solution consisting of Plasmalyte A. The pH of a 40 ml aliquot sample of each of the five solutions was initialized with NaOH to between 8.0 and 8.4. HCl was then added dripwise to each solution and the resulting pH measured every 0.2 ml. The pH measurements obtained are illustrated in FIG. 1, in which the vertical axis represents pH and the horizontal axis represents the concentration of HCl. The curves of FIG. 1 clearly show that in the pH range 8 to 7, all aminosulfonic acids tested had buffer strength values far greater than bicarbonate when using comparable 0.1 molar solutions. Thus, the titration curves of FIG. 1 display the superior buffer strength of aminosulfonic acids as compared to bicarbonate.

Figure 2:
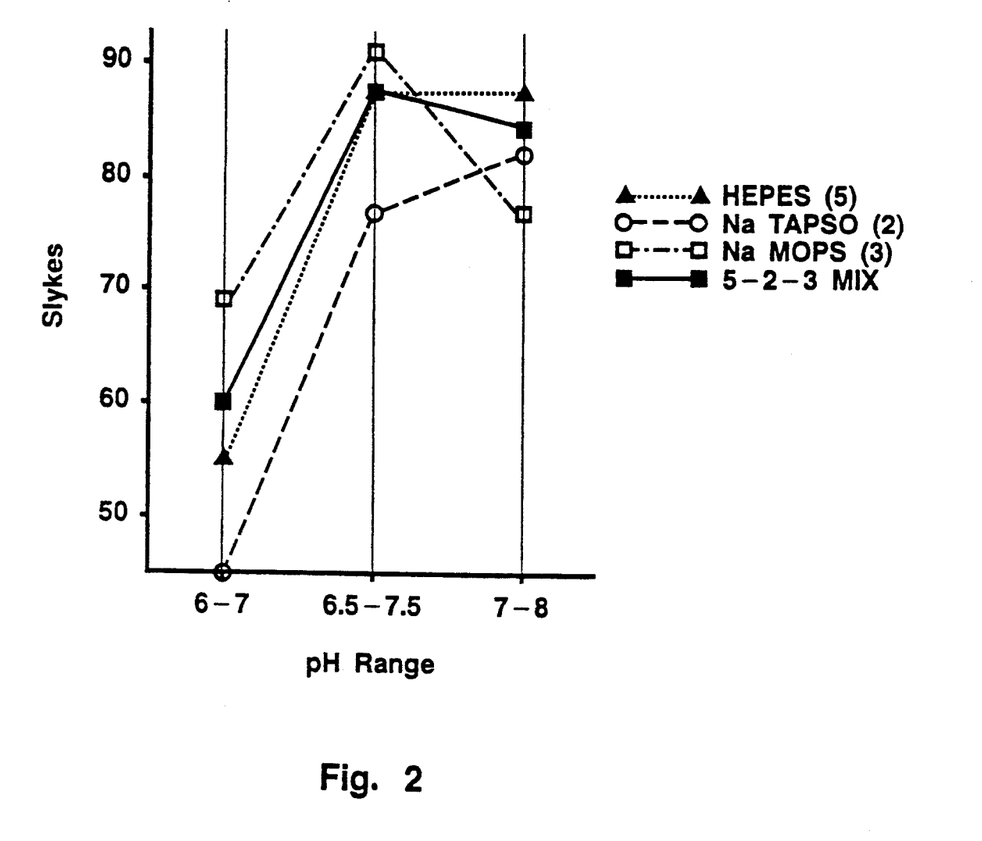
FIG. 2 is a graph containing four curves comparing the buffer strength of three aminosulfonic buffers and the buffer strength of a mixture of the three aminosulfonic buffers over a range of 3 pH units.

FIG. 2 illustrates a second preliminary laboratory test. The broad range of buffer strength with ASAs is illustrated in FIG. 2, in which the vertical axis represents buffering capacity and the horizontal axis represents the span of pH units tested. The four buffering capacity curves shown in FIG. 2 illustrate the buffering strength over 3 pH units of (1) a solution of HEPES; (2) a solution of NaTAPSO; (3) a solution of NaMOPS; and (4) a solution comprising five parts HEPES, two parts NaTAPSO and three parts NaMOPS. All four solutions were of a 0.2M concentration, with each datum point the mean of three determinations. The flat character of the fourth curve illustrates that the buffer strength of the HEPES/NaTAPSO/NaMOPS solution is relatively steady. In comparison, the vertically increasing aspects of the first, second and third curves illustrate that the buffer strength of each solution changes more definitively at different pH levels, illustrating that the pH range of buffer strength is not as broad as the 5:2:3 composition. In short, since the HEPES/NaTAPSO/NaMOPS solution is the flattest, the HEPES/NaTAPSO/NaMOPS solution exhibits the broadest range of buffer effectiveness as compared to the HEPES, the NaTAPSO, or the NaMOPS solutions. The enhanced buffering effect of the HEPES/NaTAPSO/NaMOPS solution was not expected and supports the concept that a mixture of different ASAs and their salts can be used to create a broad effective range around a specific pKa to treat a patient with specific acid-base disturbance due to disease or trauma.

To determine whether the aminosulfonic acids were sufficiently non-toxic to warrant further development of the present invention a test was performed using rats. Three solutions were made using TAPSO, HEPES, and a 50-50 mix of the two in 0.35M strengths. A control solution was made using balanced salt solutions to which was added enough urea to bring the osmolar strength to 471 mOsm. The pH of all solutions was then adjusted to 7.4 or 7.5 by adding 1N HCL or 1N NaOH as required. Osmolality of the three buffer solutions varied from 465 to 485 mOsm. The volume of the injections was equal to 8% of body weight in grams, and contained 25 meq/kg of rat weight infused in less than one hour.

Infusion was performed using a mechanized adjustable syringe compressor. Injection times varied from 48 to 58 minutes. No animal appeared to have acute or severe circulatory distress as a result of the infusion. After the infusion, the animals were allowed to recover and were then observed for a period of one week or until their demise if that occurred earlier. Rat survival following these infusions is displayed in the following table:

TABLE

| Solution description | | | Survived | Died |
|---|---|---|---|---|
| 1. BSS-Urea | | pH 7.4, mOs 471 | 6 | 0 |
| 2. HEPES | 0.35M, | pH 7.4, mOs 485 | 4 | 1 |
| 3. TAPSO | 0.32M, | pH 7.5, mOs 471 | 4 | 1 |
| 4. HEPES-TAPSO | 0.35M | pH 7.5, mOs 465 | 5 | 0 |

Summarizing the toxicity studies in rats, 2 of 15 rats receiving the hyperosmolar infusion containing 10 times the estimated clinical dose of an aminosulfonic acid buffer delivered in a period of less than one hour succumbed to the procedure. This degree of safety in a vertebrate, with such a low mortality rate after a rapid large intravenous injection, was quite unexpected. The unexpected survival rate prompted subsequent laboratory experimentation by the inventor of the present invention which led to the synthetic buffering composition and aqueous solutions as well as methods for their administration.

Presently preferred embodiments of the present inventions and many of its improvements have been described with a degree of particularity. It should be understood that this description has been made by way of preferred examples, and that the invention is defined by the scope of the following claims.

What is claimed is:

1. A method for treating acidosis in a patient, said method comprising administering to a patient in need thereof an effective amount of a buffering solution, said buffering solution comprised of:
   (a) water;
   (b) at least one N-substituted aminosulfonic acid selected from the group consisting of BES, DIPSO, HEPES, MOPS, MOPSO, TAPSO and TES; and
   (c) at least one sodium salt of an N-substituted aminosulfonic acid selected from the group consisting of NaBES, NaDIPSO, NaHEPES, NaMOPS, NaMOPSO, NaTAPSO and NaTES where the N-substituted aminosulfonic acid from which the sodium salt is formed is different than the N-substituted aminosulfonic acid selected in (b).

2. The method defined in claim 1 wherein the buffering solution is further comprised of TRIS.

3. The method defined in claim 1 or 2 wherein the buffering solution has a pH of approximately 7.2 to 7.8 at an approximate temperature of 37° C.

4. The method defined in claim 1 or 2 wherein the buffering solution has a molar strength of approximately 0.1 to 0.5M.

5. The method defined in claim 1 or 2 wherein the buffering solution has a pKa of approximately 7.4 to 7.8 at approximately 37° C.

6. The method defined in claim 1 or 2 wherein the buffering solution has a $\Delta pK/C°$ of approximately 0.014 to 0.020.

7. The method defined in claim 1 or 2 wherein the buffering solution has an osmolality of approximately 270 to 500 mOsm.

8. The method defined in claim 1 or 2 wherein the buffering solution has a sodium ion concentration of approximately 0.035 to 0.35M.

9. The method defined in claim 2 wherein the N-substituted aminosulfonic acid is TAPSO and the sodium salt is NaDIPSO.

10. The method defined in claim 9 wherein the TAPSO is present in a concentration of approximately 47 grams per liter, the NaDIPSO is present in a concentration of approximately 37 grams per liter and the TRIS is present in a concentration of approximately 3 grams per liter.

11. A method for treating general and myocardial acidosis of a patient subjected to trauma and/or hemorrhage, said method comprising administering to a patient in need thereof an effective amount of a buffering solution, said buffering solution comprised of:
  (a) water;
  (b) at least one N-substituted aminosulfonic acid selected from the group consisting of BES, DIPSO, HEPES, MOPS, MOPSO, TAPSO and TES; and
  (c) at least one sodium salt of an N-substituted aminosulfonic acid selected from the group consisting of NaBES, NaDIPSO, NaHEPES, NaMOPS, NaMOPSO, NaTAPSO and NaTES where the N-substituted aminosulfonic acid from which the sodium salt is formed is different than the N-substituted aminosulfonic acid selected in (b).

12. A method as defined in claim 11 wherein the buffering solution is further comprised of TRIS.

13. The method defined in claim 11 or 12 wherein the buffering solution has a molar strength of approximately 0.2 to 0.5M.

14. The method defined in claim 11 or 12 wherein the buffering solution has a pKa of approximately 7.2 to 7.4 at approximately 37° C.

15. The method defined in claim 11 wherein the N-substituted aminosulfonic acid is HEPES and the sodium salts selected are NaTAPSO and NaMOPS.

16. The method defined in claim 15 wherein the HEPES, NaTAPSO and NaMOPS are present in a molar ratio of 5:4:1.

17. The method defined in claim 11 wherein the N-substituted aminosulfonic acid is HEPES, the salts selected are NaDIPSO and NaMOPS and the HEPES, NaDIPSO and NaMOPS are present in a molar ratio of 4:5:1.

18. A method to protect the blood pH and the myocardial pH of a patient suffering acute circulatory insufficiency associated with or due to decreased coronary blood flow, said method comprising administering to a patient in need thereof an effective amount of a buffering solution, said buffering solution comprised of:
  (a) water;
  (b) at least one N-substituted aminosulfonic acid selected from the group consisting of BES, DIPSO, HEPES, MOPS, MOPSO, TAPSO and TES; and
  (c) at least one sodium salt of an N-substituted aminosulfonic acid selected from the group consisting of NaBES, NaDIPSO, NaHEPES, NaMOPS, NaMOPSO, NaTAPSO and NaTES where the N-substituted aminosulfonic acid from which the sodium salt is formed is different than the N-substituted aminosulfonic acid selected in (b).

19. A method as defined in claim 18 wherein the buffering solution is further comprised of TRIS.

20. The method defined in claim 18 or 19 wherein the buffering solution has a pKa of approximately 7.1 to 7.4 at approximately 37° C.

21. The method defined in claim 18 or 19 wherein the buffering solution has a sodium ion concentration of up to approximately 0.150M.

22. The method defined in claim 19 wherein the N-substituted aminosulfonic acid is MOPS and the sodium salt is NaHEPES.

23. The method defined in claim 22 wherein MOPS, NaHEPES and TRIS are present in a molar ratio of 6:3:1.

24. A method for buffering the blood pH and the myocardial pH of a hypothermic patient, said method comprising administering to a patient in need thereof an effective amount of a buffering solution, said buffering solution comprised of:
  (a) water;
  (b) at least one N-substituted aminosulfonic acid selected from the group consisting of BES, DIPSO, HEPES, MOPS, MOPSO, TAPSO and TES; and
  (c) at least one sodium salt of an N-substituted aminosulfonic acid selected from the group consisting of NaBES, NaDIPSO, NaHEPES, NaMOPS, NaMOPSO, NaTAPSO and NaTES where the N-substituted aminosulfonic acid from which the sodium salt is formed is different than the N-substituted aminosulfonic acid selected in (b).

25. A method as defined in claim 24 wherein the buffering solution is further comprised of TRIS.

26. The method defined in claim 24 or 25 wherein the buffering solution has a pH of approximately 7.4 to 7.8 at an approximately temperature of 25° C.

27. A method for buffering the blood pH and the myocardial pH of a hypothermic patient during cardiac surgery with circulatory occlusion, said method comprising administering to a patient in need thereof an effective amount of a buffering solution by coronary infusion, said buffering solution comprised of:
  (a) water;
  (b) at least one N-substituted aminosulfonic acid selected from the group consisting of BES, DIPSO, HEPES, MOPS, MOPSO, TAPSO and TES; and
  (c) at least one sodium salt of an N-substituted aminosulfonic acid selected from the group consisting of NaBES, NaDIPSO, NaHEPES, NaMOPS, NaMOPSO, NaTAPSO and NaTES where the N-substituted aminosulfonic acid from which the sodium salt is formed is different than the N-substituted aminosulfonic acid selected in (b).

28. The method defined in claim 27 wherein the buffer solution is further comprised of TRIS.

29. The method defined in claim 27 wherein the N-substituted aminosulfonic acid is HEPES and the sodium salt is NaMOPS.

30. The method defined in claim 29 wherein HEPES and NaMOPS are present in a molar ratio of 3:7.

31. A method for buffering the blood pH and the myocardial pH of a hypothermic patient undergoing cardiopulmonary bypass, said method comprising adding a buffering solution to a primary fluid of a heart-lung machine, said buffering solution comprised of:

(a) water;

(b) at least one N-substituted aminosulfonic acid selected from the group consisting of BES, DIPSO, HEPES, MOPS, MOPSO, TAPSO and TES; and (c) at least one sodium salt of an N-substituted aminosulfonic acid selected from the group consisting of NaBES, NaDIPSO, NaHEPES, NaMOPS, NaMOPSO, NaTAPSO and NaTES where the N-substituted aminosulfonic acid from which the sodium salt is formed is different than the N-substituted aminosulfonic acid selected in (b).

32. The method defined in claim 31 wherein the buffer solution is further comprised of TRIS.

* * * * *